United States Patent [19]

Landgraf et al.

[11] 4,198,755

[45] Apr. 22, 1980

[54] DENTAL HANDPIECE

[75] Inventors: Hermann Landgraf, Heppenheim; Rainer Worschieschek, Lorsch, both of Fed. Rep. of Germany

[73] Assignee: Siemens Aktiengesellschaft, Berlin & Munich, Fed. Rep. of Germany

[21] Appl. No.: 813,448

[22] Filed: Jul. 7, 1977

[30] Foreign Application Priority Data

Jul. 23, 1976 [DE] Fed. Rep. of Germany ....... 2633223

[51] Int. Cl.² .............................................. A61C 1/12
[52] U.S. Cl. .................................................... 433/126
[58] Field of Search ................................ 32/28, 26, 27

[56] References Cited

U.S. PATENT DOCUMENTS

| 3,252,719 | 5/1966 | Borden | 32/27 |
| 3,858,323 | 1/1975 | Flatland | 32/27 |
| 3,936,940 | 2/1976 | Loge | 32/27 |
| 4,007,529 | 2/1977 | Fleer | 32/27 |
| 4,075,761 | 2/1978 | Behne et al. | 32/27 |

Primary Examiner—Louis G. Mancene
Assistant Examiner—John J. Wilson

Attorney, Agent, or Firm—Hill, Van Santen, Steadman, Chiara & Simpson

[57] ABSTRACT

A dental handpiece having a drive section and a detachably connected grip section with a working instrument with at least one cooling medium line for conveying a cooling medium to the area of the instrument characterized by the grip section including at least a first and second part engaged with each other for relative rotation therebetween with each part having a segment of a fluid passage for each of the cooling mediums line with the second part being non-rotatably connected with the drive section and a rotatable fluid connection disposed between the first and second parts so that the grip section is free to rotate relative to the drive section of the handpiece and the second part. In one embodiment of the invention, the fluid connection is formed by an annular groove in one of the first and second parts with a port in the other of said parts axially aligned and sealed therewith by sealing rings. In another embodiment of the invention, the fluid connection is formed by flexible tube loosely received in an annular space in the grip section which tube interconnects the segments of the two parts.

7 Claims, 6 Drawing Figures

U.S. Patent   Apr. 22, 1980   Sheet 1 of 2   4,198,755
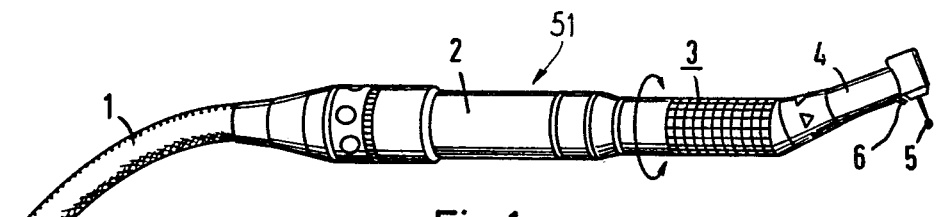
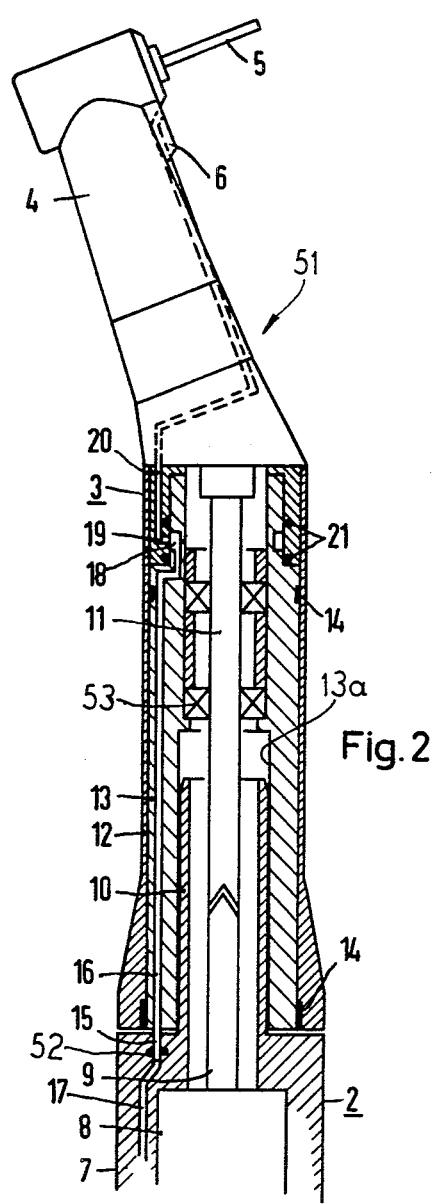
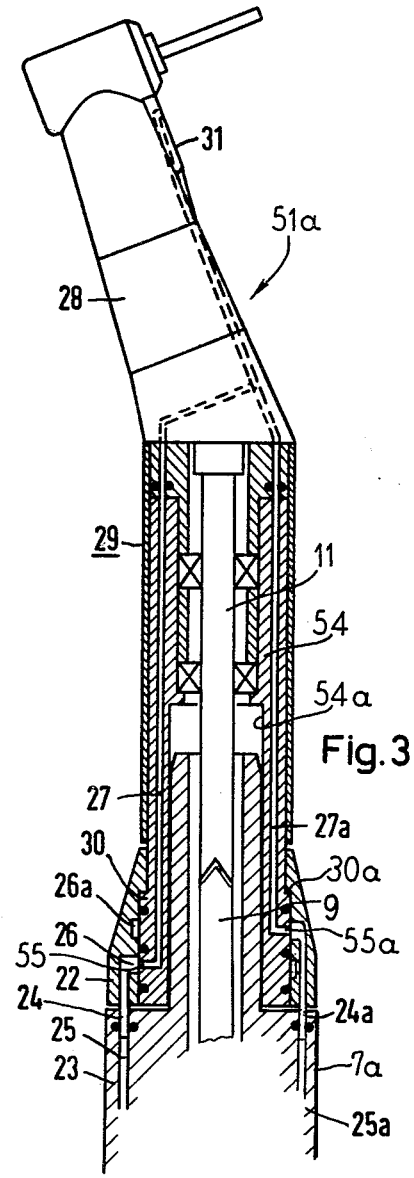

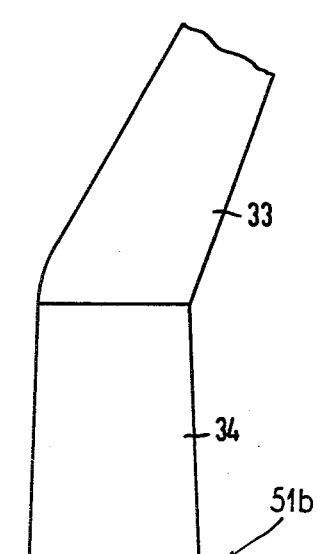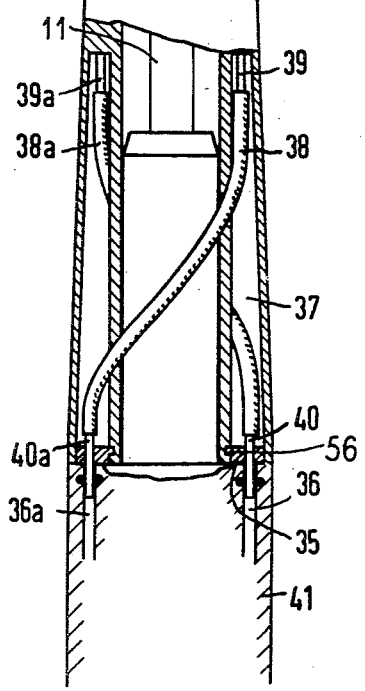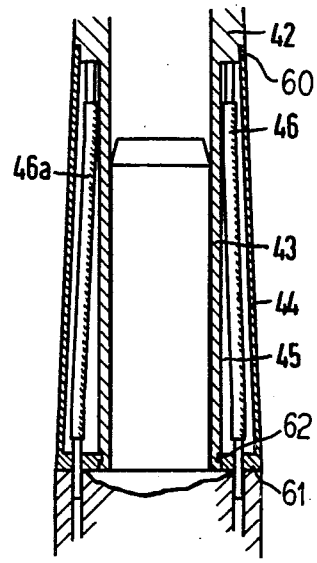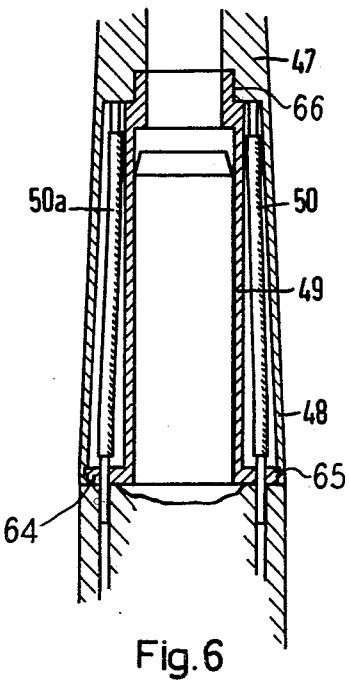
Fig. 4  Fig. 5  Fig. 6

DENTAL HANDPIECE

BACKGROUND OF THE INVENTION

1. Field of the Invention

The present invention is directed to a dental handpiece, which has a grip section, which has a head section at one end for supporting a working instrument, such as a dental burr or drill, for rotation, and is coupled for relative rotation to a drive section containing a motor for rotating the dental instrument. The dental handpiece has at least one coolant line for supplying a coolant for discharge to the area of the dental instrument and each coolant line is formed by passages in the drive section and grip section which are interconnected as the grip section is coupled onto the drive section.

2. Prior Art

A dental handpiece, which has a grip section, which is coupled onto a drive section for relative rotation with the grip and drive sections having passages coacting to form at least one coolant line for conveying a cooling medium to the area of a dental instrument, is disclosed in U.S. Pat. No. 3,936,940. In this handpiece, a connection between the passages of the drive section and grip section is formed by an annular groove provided in one of the two sections, which is in communication with a port in the other section and the connection is sealed by a pair of O-rings received in O-ring grooves. In the patent, two embodiments of the fluid connection provide the port, the annular or ring groove and the O-rings on parts which are telescopically received on each other during the connection of the grip section to the drive section. In the third embodiment, the fluid connection is formed by the annular groove, port and the O-ring grooves and O-rings being disposed on plane surfaces, which extend radially to the axis of the drive shaft of the drive section. In each embodiment, the O-rings are carried on the drive section and the coupling and decoupling of the grip section onto the drive section connects and disconnects the rotatable connection.

Thus, in the handpiece such as disclosed in this U.S. patent, the O-rings are subjected to stresses during the coupling and decoupling of a grip section from the drive section and in several embodiments, the O-rings are also subjected to a twisting stress. Since a dentist as a rule will utilize a single drive section for a dental handpiece with several different grip sections, which have different gearing arrangement to either step up or step down the speed or rotation for the tool, the drive section is thus the most frequently used part. Thus, the sealing rings, which are carried on the drive section, are subjected to stresses occurring during coupling and decoupling of each grip section on the drive section. Since coupling and decoupling of the grip section frequently occurs, the sealing rings are subjected to particularly heavy wear, which can lead to leaks occurring at the connection between the passages after a relatively short time. While one may compensate for this problem with an increase of an initial radial tension on the sealing rings, such an increase would also increase the friction between the two rotatable sections and thus decrease the rotatability of the grip section on the drive section.

Since one may couple a grip section of an old construction with a drive section, which is provided with a cooling medium connection adjacent to the guide member, even greater wear of the sealing rings may occur. For example, grip sections of an older type often do not have beveled or chamfered edges to facilitate their mounting on the guide member and thus these older type grip sections will increase the wear or chance of damage to the sealing rings on the drive section.

In addition to the disadvantages of relatively heavy wear of the sealing rings in the previously known type of handpiece, the occurrence of a leak due to wear may not be recognized by the user of the handpiece. While a leakage at one of the two sealing rings will allow the liquid to flow to an external surface to be noticed, leakage at the other ring will allow the cooling medium to penetrate into the interior of either the grip section or the drive section and thus into portions of the drive train such as bearings of the drive train without the operator being aware of such a leak.

An additional disadvantage of the rotatable connection of the dental handpiece of the above mentioned patent is the fact that while the grip section is disconnected from the drive section, the sealing rings are not protected against soiling or other damage. This danger particularly exists when the grip section has been uncoupled from the drive section for a long time, which would occur while sterilizing the grip section or while storing the grip section in a sterile condition.

SUMMARY OF THE INVENTION

The present invention is directed to providing a dental handpiece having a drive section with a detachably coupled grip section wherein the rotatable connection of the passages of each of the coolant lines is less susceptible to the problems which occur with the prior art devices. In addition, the sealing rings are subjected to less wear and the connection of the passages of the cooling medium lines is less susceptible to leaks, which, if they occur, are less damaging to the dental handpiece.

To accomplish these tasks, the present invention is directed to an improvement in a dental handpiece having a drive section and a grip section, said drive section having a housing containing a motor and a guide member encircling the drive shaft of the motor, said grip section at one end having a head section supporting a working instrument for rotation, said working instrument being rotated by a drive shaft carried in the grip section, said grip section at the other end having means coacting with the guide member to couple the grip section and drive section together with the drive shaft of the motor engaged with the drive shaft of the grip section, said handpiece having at least one cooling medium line for conveying a cooling medium to the area of the instrument, each cooling medium line including a passage in the drive section coupled to a passage in the grip section when the drive section and grip sections are coupled together. The improvements comprises the grip section including at least a first part and second part telescopically engaged with each other for relative rotation therebetween, one of said parts being telescopically received on said guide member to couple said sections together, each of said first and second parts having a segment of a fluid passage for each of the cooling medium lines of the handpiece, said first part being fixed to the head section and surrounding the drive shaft of the grip section, said second part having means for forming a rigid and non-rotatable connection with the drive section with each segment connected to a respective passage of the cooling medium line of the drive section, and means for forming a rotatable fluid connection between each of the segments of the first and second parts for each passage of the grip section so that the grip section is free to rotate relative to the drive section of the handpiece and the first part is free to rotate relative to the second part.

In one embodiment of the invention, the first part is a sleeve extension of the casing of the grip section, the second part is a sleeve member telescopically received in the first part and wherein the means forming the rotatable fluid connection comprises an annular groove sealed by O-rings disposed on one of said first and the second parts with the other of said first and second parts having a port axially aligned with the annular groove and in communication therewith. In another embodiment of the invention, the first part is a tubular sleeve having a shoulder adjacent the free end thereof and said second part is a sleeve member telescopically received on the first part and having a shoulder coacting with the shoulder of the first part to prevent axial removal of the second part therefrom, said means for forming a rotatable fluid connection comprises an annular groove sealed by O-rings on one of said first and second parts and a radially extending port axially aligned with said annular groove provided in the other of said first and second parts and in communication with said groove. In a third embodiment of the invention, the first and second parts defined an annular space therebetween, which space is concentric with the axis of the drive shaft of the grip section, and the means forming the rotatable fluid connection between the segments of each of the cooling medium lines comprises a flexible tube loosely disposed in the annular space and coupled to the respective segments of the first and second parts.

In each of the embodiments, the means for forming the rigid and non-rotatable connection between the second part and the drive section preferably comprises a coacting socket and a hollow prong provided for each of the segments of the second part and the passage of the drive section.

An essential advantage of the present invention comprises the fact that the means for forming the rotatable connection between the segments of the first and second parts is disposed in the grip section, which is a less used part and, therefore, components of the means such as the sealing rings are subjected to less wear. In addition, since the means for forming the rotatable connection is disposed in the grip section, it is not subject to disassembly during decoupling of the grip section from the drive section of the handpiece.

BRIEF DESCRIPTION OF THE DRAWINGS

FIG. 1 is a perspective view of a dental handpiece in accordance with the present invention;

FIG. 2 is an enlarged partial cross-sectional view of the handpiece of FIG. 1;

FIG. 3 is a partial cross-sectional view of a second embodiment of the handpiece in accordance with the present invention;

FIG. 4 is a partial cross-sectional view of a third embodiment of the handpiece in accordance with the present invention;

FIG. 5 is a partial view illustrating a modification of the third embodiment of the present invention; and FIG. 6 is a partial cross-sectional view illustrating another modification of the third embodiment.

DESCRIPTION OF THE PREFERRED EMBODIMENTS

The principles of the present invention are particularly useful in a dental handpiece generally indicated at 51 in FIG. 1. The dental handpiece 51 has a drive section 2 coupled at one end to a supply hose 1 and a grip section 3 coupled to the opposite end of the drive section 2 for rotation as illustrated by the arrow. The grip section 3 at an end opposite to the end coupled to the drive section 2 has a head section 4, which is illustrated as being an angled off head section and supports a dental instrument or tool 5 which may be a drill or burr. To provide a cooling medium for the tool 5, the handpiece 51 has at least one cooling medium line which conveys the cooling medium such as air, water or a mixture of air and water from the supply line 1 through the internal passages in the sections 2 and 3 for discharge from a tube or port 6 into the area of the dental instrument such as the drill 5.

As best illustrated in FIG. 2, the drive section 2 has a housing 7 which receives a drive motor 8 that may be either an electrical or air motor. The drive motor 8 has a drive or output shaft 9, which is encircled by a guide member 10, which is illustrated as a tubular extension of the housing 7. For each cooling medium line of the handpiece 51, the housing 7 will have a passage such as 17, which terminates in a socket having a sealing ring 52.

The grip section 3 has a drive shaft 11, which is coupled to the drive shaft 9 of the motor 8 when the grip section 3 is coupled onto the drive section 2. The drive shaft 11 is part of a gear train, which either directly drives the tool 5 or includes a gear arrangement, which will either step up or step down the number of revolutions of the tool 5 relative to the shaft 11. This gear arrangement is disposed within the interior of the grip section 3.

The grip section 3 has a first part 12, which is attached to the head section or portion 4 and is an outer casing of a portion of the grip section 3. A second part 13 is a sleeve-like tubular member, which is telescopically received and fixed in the first part 12 and supported for rotation therewith by bearings 14. As illustrated, the part 13 has a socket 13a, which telescopically receives the guide member 10 and coacts therewith to form a coupling between the grip section and the drive section 2. In addition, the part 13 is provided with bearings such as 53 to rotatably support the drive shaft 11 of the grip section 3.

The member 13 has a segment 16 of an internal passage of the grip section 3. As illustrated, the segment 16 is provided with a hollow prong 15, which is received in the socket having the sealing ring 52 to couple the segment 16 to the passage 17 in the drive section 2 and to fix the second part 13 with a fixed and non-rotatable connection to the drive section 2.

The segment 16 at an opposite end terminates in an annular groove 18, which is sealed by a pair of axially spaced O-rings 21 and is axially aligned with a radially extending port 19 of the first part 12 to form a rotatable fluid connection. The port 19 is part of a segment 20 of an internal passage of the grip section 3 which passage extends to the nozzle or port 6 adjacent the tool 5.

Due to the prong 15 and socket connection, the second part 13 is fixed to the drive section 2 as the part 12 and the remaining parts of the grip section 3 are free to rotate thereon. Thus, the rotatable fluid connection formed by the groove 18, the port 19 and the O-rings 21 is disposed within the grip section 3 and is not disturbed during uncoupling of the grip section 3 from the drive section 2. Since the rotatable fluid connection is not disturbed during uncoupling of the grip section 3 from the drive section 2, parts, such as the O-rings 21, are subjected to substantial less wear than the O-rings of the prior art devices.

It should be noted that while the segment 16 is illustrated as having a prong received in a socket of the drive section 2, these parts can be reversed. In a similar manner, the position of the port 19 and the groove 18 can be reversed so that the port is provided on the second part 13 and the groove is provided in the first part 12 and axial alignment therewith.

An embodiment of a handpiece is generally indicated at 51a in FIG. 3 and includes a drive section 23 and a grip section 29. The drive section 23 has a housing 7a, which contains a motor having a drive shaft 9 and the housing 7a has a guide member which surrounds the drive shaft 9. As illustrated, the housing 7a has two passages 25 and 25a for two separate cooling medium lines such as a water line and an air line, which passages 25 and 25a terminate in sockets similar to the socket of the passage 17 in the embodiment of FIG. 2.

The grip section 29 has a first part 54, which is a tubular member attached to a head section or portion 28 and is provided with a socket 54a for telescopically receiving the guide member 10a to form a connection between the grip section 29 and the drive section 23. The first part 54 has a pair of segments 27 and 27a for internal fluid passages which segments extend parallel to the axis of the drive shafts 9 and 11 and terminate in radial ports 55, 55a in a thickened end portion 30 of the first part or member 54. As illustrated, the segments 27 and 27a at the other end extend into the head section 28 and are combined so that the two cooling mediums are directed through a port or nozzle 31 at the area of the tool.

A second part or member 22 is an annular sleeve-like member telescopically received on the first part 54 and is provided with a radial inwardly extending shoulder which engages a shoulder 30a of the end member 30 to prevent axial removal of the part 22 from the first part 54. The second part 22 has two segments with prongs 24, 24a, which are received in the sockets of the passages 25, 25a to fix the second part 22 onto the housing of the drive section 23. The segments of the second part 22 terminate in axially spaced, annular grooves 26 and 26a, which are axially aligned with the ports 55 and 55a and sealed by the O-rings. Due to the arrangement of the pair of rotational fluid connections formed by the grooves 26 and 26a and the ports 55 and 55a, the first part 54 can be rotated relative to the fixed second part 22 so that the grip section 29 is rotatable relative to the drive section 23.

As in the embodiment of FIG. 2, the prongs such as 24 and 24a can be provided on the drive section 23 to be received in sockets formed in the segments of the second part 22. In addition, the annular grooves 26 and 26a can be formed on the first part 54 with the radial ports being formed in the second part 22, if desired.

A third embodiment of the handpiece of the present invention is generally indicated at 51b in FIG. 4. The handpiece 51b includes a grip portion 34 having a head portion 33 coupled to a drive section 41. The grip section 34 has a first member or part, which is integral with the rest of the housing for the grip section and has an annular-shaped concentric groove whose open end is closed by a second part 35, which is a disk-shaped part, to form an annular enclosed space 37 which is concentric with the drive shafts such as 11. The first part has segments provided with hollow prongs 39 and 39a and the second part 35 has a pair of segments, which receive prongs 40 and 40a.

To form a rotational fluid connection between the segments such as 39 and 40a a flexible tube such as 38, which is longer than the axial distance between the prongs 39 and 40a, is loosely received in the annular space 37 and connected to the prongs 39 and 40a. In a similar manner, flexible tube 38a interconnects the prongs 39a and 40.

As in the second embodiment of FIG. 3, the drive section 41 has a housing which is provided with a pair of passages 36 and 36a for two separate types of cooling medium which passages terminate in sockets which receive the other end of the prongs 40 and 40a. The housing of the drive section 41 will contain a motor and a drive shaft which is engaged by the drive shaft 11 of the grip section 34 as the grip section 34 is coupled onto the drive section 41. Due to the prongs 40 and 40a being received in the sockets of the passage 36 and 36a, the second part 35 is fixed in a non-rotatable manner to the drive section 41; however, the first part and the rest of the grip section 34 are free to rotate relative to the drive section 41 and the second part 35 due to the flexibility of the hoses or tubes 38 and 38a.

To prevent the part 35 from becoming disengaged from a position closing the annular groove of the first part, it may be provided with means such as an inwardly extending annular ridge which is received in an annular groove 56 that is provided in the first part. An advantage of this embodiment is that due to the use of flexible tubes 38 and 38a, leaks will hardly occur in the area of the relatively rotatable parts.

Instead of forming the annular space 37 by providing an annular concentric groove in the first part, the first and second parts may be formed as sleeve-like members, which are telescopically received with sufficient spacing therebetween to form the annular space 37. For example, in FIG. 5 the grip section 42 has a first part 43 which has a sleeve portion and the second part 44 is an outer sleeve portion which has one end engaging an annular shoulder 60 of the first portion and the other end provided with an inwardly extending flange 61 having an annular projection received in a groove 62 of the sleeve portion 43 of the first part. Due to the annular flange 61, an annular space 45 is provided therebetween for loosely receiving tubes or flexible hoses 46 and 46a which interconnect the segments of the tube parts which segments may be formed by hollow prongs. As in the previous embodiments, the hollow prong of the second part 44 are used to fixedly attach the second part onto the drive section.

In the modification illustrated in FIG. 6, the housing of the grip section 47 has a first part formed by an axially extending sleeve 48 that forms an outer casing of the grip section. A second part 49 is a tubular sleeve having an outwardly extending annular flange 64 with an annular projection received in an annular groove 65 of the sleeve portion 48 and a stepped portion forming an annular rotatable connection at 66. Due to this spacing between the first and second parts 48 and 49, an annular concentric space is provided for loosely receiving flexible tubes or hoses 50 and 50a which interconnect the segments of the first part 48 with the prongs that form the segments in the second part 49, which prongs fixedly attach the second part onto the drive section.

It should be noted that while the annular groove, a pair of O-rings, and radial ports between the first and second parts of the embodiments of FIGS. 2 and 3 provide unlimited relative rotation between the grip portion and the drive portion, the flexible hoses of the embodiment of FIGS. 4, 5 and 6 will only provide a limited relative rotation. The amount of the limited relative rotation will be determined by the excess length of the hoses such as 50, 50a over the axis distance between the prongs of the first and second parts.

Although various minor modifications may be suggested by those versed in the art, it should be understood that we wish to embody within the scope of the patent warranted hereon, all such modifications as reasonably and properly come within the scope of our contribution to the art.

We claim:

1. In a dental handpiece having a drive section and a grip section, said drive section having a housing containing a motor and a guide member encircling a drive shaft of the motor, said grip section at one end having a head section supporting a working instrument for rotation, said working instrument being rotated by a drive shaft carried in the grip section, said grip section at the other end having means coacting with the guide member to releasable couple the grip section and drive section together with the drive shaft of the motor engaged with a drive shaft of the grip section, said handpiece having at least one cooling medium line for conveying a cooling medium from a supply hose to the area of the instrument, each cooling medium line including a passage in the drive section coupled to a passage in the grip section when the drive section and grip sections are coupled together, the improvements comprising the grip section including at least a first part and second part being telescopically engaged with each other for relative rotation therebetween, one of said parts being telescopically received on said guide member to couple said sections together, each of said first and second parts having a segment of a fluid passage for each of the cooling medium lines of the handpiece, said first part being fixed to the head section and surrounding the drive shaft of the grip section, said second part having means forming a rigid and non-rotatable connection with the drive section with each segment connected to the respective passage of the cooling medium line of the drive section, and means for forming a rotatable fluid connection between each of the segments of the first and second parts for each passage of the grip section so that the grip section is free to rotate relative to the drive section of the handpiece.

2. In a dental handpiece according to claim 1, wherein the means for forming the rigid and non-rotatable connection between the second part and the drive section comprises a coacting socket and hollow prong provided for each segment of the second part and the respective passage of the drive section.

3. In a dental handpiece according to claim 1, wherein the first part is a sleeve extension of the casing of the grip section, said second part is said one part, which is telescopically received on said guide member, and is a sleeve member telescopically received in the first part, and wherein the means for forming a rotatable fluid connection comprises an annular groove sealed by O-rings disposed on one of said first and second parts, with the other of said first and second parts having a port axially aligned with the annular groove and in communication therewith.

4. In a dental handpiece according to claim 1, wherein the first part is said one part, which is telescopically received on said guide member, and is a tubular sleeve having a shoulder adjacent a free end thereof, said second part being a sleeve member telescopically received on the first part and having a shoulder coacting with the shoulder of the first part to prevent axial removal of the second part therefrom, and said means for forming a rotatable fluid connection comprises an annular groove sealed by O-rings on one of said first and second parts and a radially extending port axially aligned with said annular groove provided in the other of said first and second parts and in communication with said groove.

5. In a dental handpiece according to claim 1, wherein said first and second parts define an annular space therebetween and concentric with the axis of said drive shaft, and wherein said means forming a rotatable fluid connection between the segments of each of the cooling medium for each cooling medium line comprises a flexible tube loosely disposed in the annular space and coupled to the respective segment of the first and second parts.

6. In a dental handpiece according to claim 5, wherein said annular space comprises an annular groove formed in the first part, said second part being an annular disk closing said groove.

7. In a dental handpiece according to claim 5, wherein each of said first and second parts comprise sleeve-shaped members telescopically arranged together, the inner of said two parts engaging the outer part at two axially displaced positions to provide said annular space.

* * * * *